(12) United States Patent
Gerling et al.

(10) Patent No.: US 9,513,230 B2
(45) Date of Patent: Dec. 6, 2016

(54) APPARATUS AND METHOD FOR OPTICAL INSPECTION, MAGNETIC FIELD AND HEIGHT MAPPING

(71) Applicant: KLA-Tencor Corporation, Milpitas, CA (US)

(72) Inventors: John Gerling, Livermore, CA (US); Edward Wagner, San Jose, CA (US); Mehran Nasser-Ghodsi, Hamilton, MA (US); Garrett Pickard, Mountain View, CA (US); Tomas Plettner, San Ramon, CA (US); Robert Haynes, Pleasanton, CA (US); Christopher Sears, San Jose, CA (US)

(73) Assignee: KLA-TENCOR CORPORATION, Milpitas, CA (US)

( * ) Notice: Subject to any disclaimer, the term of this patent is extended or adjusted under 35 U.S.C. 154(b) by 261 days.

(21) Appl. No.: 14/095,918

(22) Filed: Dec. 3, 2013

(65) Prior Publication Data

US 2014/0218503 A1     Aug. 7, 2014

Related U.S. Application Data

(60) Provisional application No. 61/737,273, filed on Dec. 14, 2012.

(51) Int. Cl.
   *G01N 27/82*    (2006.01)
   *G01N 21/95*    (2006.01)
   (Continued)

(52) U.S. Cl.
   CPC ............. *G01N 21/9501* (2013.01); *G01B 7/02* (2013.01); *G01B 7/102* (2013.01); *G01B 7/28* (2013.01);
   (Continued)

(58) Field of Classification Search
   CPC ...... G01N 21/9501; G01N 27/82; G01B 7/02; G01B 21/02
   See application file for complete search history.

(56) References Cited

U.S. PATENT DOCUMENTS

| 5,822,449 A | 10/1998 | Kobayashi et al. |
| 6,496,270 B1 | 12/2002 | Kelley et al. |
| (Continued) | | |

FOREIGN PATENT DOCUMENTS

| JP | 2005005983 A | 1/2005 |
| JP | 2010033593 A | 2/2010 |

OTHER PUBLICATIONS

Co-Pending U.S. Appl. No. 61/737,273, entitled "Apparatus and Method for Optical Inspection, Magnetic Field and Height Mapping" to John Gerling et al., filed Dec. 14, 2012.
(Continued)

*Primary Examiner* — Dave Czekaj
*Assistant Examiner* — Nam Pham
(74) *Attorney, Agent, or Firm* — Joshua D. Isenberg; JDI Patent

(57) ABSTRACT

A metrology system is configured to provide visual inspection of a workpiece, three-dimensional magnetic field map, and height measurement. A stage is configured to bring points of interest at the workpiece under the desired tool for measurement. The optical field, magnetic field, and height information can be used independently or together in order to correlate defects in the manufacturing process of the workpiece. This abstract is provided to comply with rules requiring an abstract that will allow a searcher or other reader to quickly ascertain the subject matter of the technical disclosure. It is submitted with the understanding that it will not be used to interpret or limit the scope or meaning of the claims.

22 Claims, 3 Drawing Sheets

(51) Int. Cl.
*G01B 7/28* (2006.01)
*G01B 11/24* (2006.01)
*G01N 21/956* (2006.01)
*G01B 7/06* (2006.01)
*G01B 11/06* (2006.01)
*G01B 7/02* (2006.01)
*G01B 21/02* (2006.01)
*H04N 5/225* (2006.01)
*H04N 7/18* (2006.01)

(52) U.S. Cl.
CPC ........... *G01B 11/0608* (2013.01); *G01B 11/24* (2013.01); *G01B 21/02* (2013.01); *G01N 21/956* (2013.01); *G01N 27/82* (2013.01); *H04N 5/2251* (2013.01); *H04N 7/18* (2013.01)

(56) References Cited

U.S. PATENT DOCUMENTS

| | | | |
|---|---|---|---|
| 6,781,370 B1* | 8/2004 | Hinken | G01N 25/72 324/224 |
| 6,947,852 B2 | 9/2005 | Hess et al. | |
| 6,977,791 B2 | 12/2005 | Zhu et al. | |
| 7,075,741 B1 | 7/2006 | Soetarman et al. | |
| 7,397,621 B2 | 7/2008 | Hou et al. | |
| 2002/0033695 A1* | 3/2002 | Xiao | G01R 33/0385 324/244 |
| 2002/0042153 A1* | 4/2002 | Holcman | H01L 22/34 438/14 |
| 2004/0027584 A1* | 2/2004 | Dulman | G01B 11/2441 356/511 |
| 2007/0031993 A1 | 2/2007 | Nemets et al. | |
| 2009/0025463 A1* | 1/2009 | McFarland | G01B 21/045 73/104 |
| 2010/0205699 A1* | 8/2010 | Tachizaki | B82Y 15/00 850/47 |

OTHER PUBLICATIONS

International Search Report and Written Opinion for International Application No. PCT/US2013/074839, dated Mar. 25, 2014.

\* cited by examiner

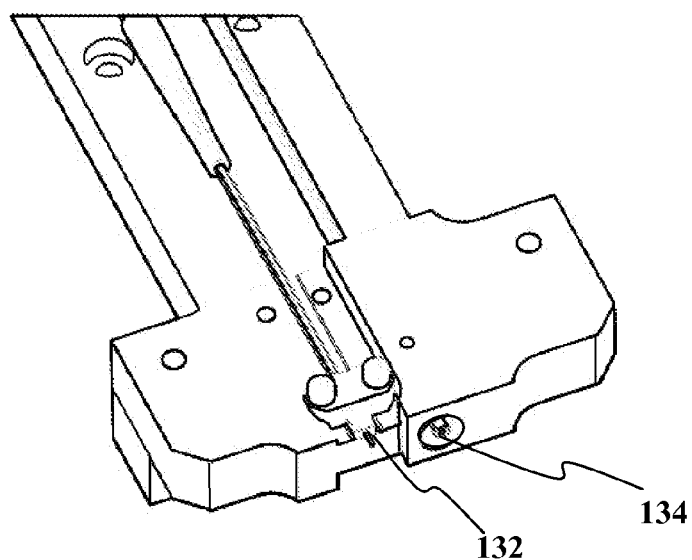
FIG. 2
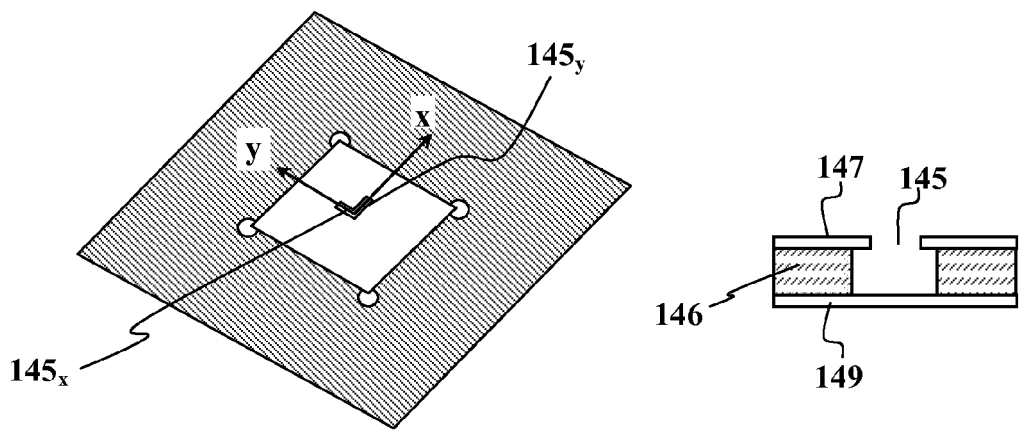
FIG. 3A                    FIG. 3B

APPARATUS AND METHOD FOR OPTICAL INSPECTION, MAGNETIC FIELD AND HEIGHT MAPPING

CLAIM OF PRIORITY

This application is a nonprovisional of and claims the priority benefit of commonly owned, U.S. Provisional Patent Application No. 61/737,273, to John Gerling et al., filed Dec. 14, 2012, and entitled "APPARATUS AND METHOD FOR OPTICAL INSPECTION, MAGNETIC FIELD AND HEIGHT MAPPING" the entire disclosures of which are incorporated herein by reference.

FIELD OF THE INVENTION

Embodiments of the present invention relate to metrology systems employed in fabrication processes, and more particularly, to an apparatus and a method for obtaining optical images, magnetic field and height topology maps for an electromagnet or permanent magnet.

BACKGROUND OF THE INVENTION

Monitoring and evaluation of fabrication processes on the circuit structures and other types of structures is necessary to ensure the manufacturing accuracy and to ultimately achieve the desired performance of the finished electronic device. With the development trend in miniature devices, the ability to examine microscopic structures and to detect microscopic defects becomes crucial to the fabrication processes.

Various technologies and methods of defect inspection on patterns or structures formed on semiconductor wafers or magnetic arrays have been developed and employed with varying degrees of success. For example, optical inspection methods employ optical inspection tools such, as an optical microscope, the inspect pattern shapes for defects. This type of device usually involves collecting radiation emitted from a target or scattered by a target from an incident beam of radiation directed at the structure. The collected radiation is converted to signals that can be measured or used to form an image. Such measurements or images can be used to determine various characteristics, such as the profile of the structure. Additionally, for wafer topography, electric sensors, such as capacitive sensors, have been employed to measure variations in substrate height. Such sensors detect changes in capacitance due to variations in topography as a sensor element is scanned across a target. The height of the sensor is typically controlled by a height transducer such as a piezoelectric element, which keeps the sensor element at a fixed height above the target structure. Changes in the signals that drive the height transducer can be analyzed to determine the profile of the structure.

With respect to magnetic samples, magnetic microscopy has been widely used in many areas of research for imaging and characterizing the samples. Suitable applications for the magnetic microscope include failure analysis, fault isolation, inspection of semiconductor integrated circuit, manufacturing monitoring and other biological, chemistry, physics and materials research applications. Specifically, many physical objects (e.g., conductors or semiconductors) generate magnetic fields near the objects surfaces when a current flows inside them. The magnetic microscope can obtain images of the magnetic fields by scanning a magnetic sensor on the surface of the object of interest. With the images of the magnetic fields, it is possible to reconstruct the path followed by the currents and consequently localize any defects. Additionally, the magnetic field is not perturbed by non-ferromagnetic materials, and thus, a map of the currents may be produced without de-processing the device. Accordingly, it avoids the risk of losing the defect by de-packaging the component in the localization stage. There are currently a number of techniques for imaging magnetic fields at surfaces. The conventional scanning magnetic microscope has a microscopic field sensor, typically a superconducting quantum interference device (SQUID), a Hall probe or simply a magnetic tip. This type of microscope scans the magnetic sensor relative to a sample to obtain a local field image. The magnetic sensor is typically controlled by a magnetic transducer such as a piezoelectric element.

It is within this context that aspects of the present disclosure arise.

SUMMARY

According to aspects of the present disclosure, a system comprises an optical inspection tool configured to provide image information of a sample, a magnetic sensor configured to provide magnetic field information of the sample, and a height sensor configured to provide height information of the sample. The optical inspection tool, the magnetic sensor and the height sensor are mounted to a system head. A stage is configured to hold the sample. The stage and system head are configured to move relative to each other. The stage includes one or more fiducial features for determining relative positions of the optical inspection tool, the magnetic sensor and the height sensor.

The system may further include a processor coupled to the optical inspection tool, the magnetic sensor, and the height sensor. The processor may be configured to collect the image information, the magnetic field information and the height information of the sample and use alignment information from the one or more fiducial features to determine one or more relative offsets between two or more of the optical inspection tool, the magnetic sensor, and the height sensors.

The processor may be configured to use the or more relative offsets to obtain magnetic field and sample height information at a given position on the sample In some implementations, the optical inspection tool is an optical microscope, scanning capacitance microscope or scanning electron microscope.

In some implementations, the magnetic sensor is a Hall probe, magnetoresistive sensor, giant magnetoresistance sensor (GMR) or magneto optical Kerr effect (MOKE).

In some implementations, the height sensor is a capacitive sensor, laser interferometry, inductive sensor, drop gauge, atomic force microscope (AFM), scanning tunneling microscope (STM) or stylus profilometer.

In some implementations, the magnetic sensor and the height sensor are provided in a bracket mounted on the system head.

According to certain aspects of the disclosure, a method comprises imparting relative movement between a stage which holds a sample and a system head. An optical inspection tool, a magnetic sensor and a height sensor are mounted to the system head. Relative positions of the optical inspection tool, the magnetic sensor and the height sensor are determined with one or more fiducial features on the stage.

The method may further include imparting relative movement between a stage which holds a sample and a system head. An optical inspection tool, a magnetic sensor and a height sensor are mounted to the system head. Relative positions of the optical inspection tool, the magnetic sensor and the height sensor are determined with one or more fiducial features on the stage.

The method may also further include acquiring image information of the sample with the optical inspection tool; acquiring magnetic field information of the sample with the magnetic sensor; acquiring height information of the sample with the height sensor; and using the or more relative offsets to obtain magnetic field and sample height information at a given position on the sample In some implementations of the method, the magnetic sensor and the height sensor are provided in a bracket mounted on the system head.

In some implementation of the method, the calibration device includes an optical calibration slide having features of known dimension for position or dimensional calibration for the optical inspection tool.

In some implementation of the method, the calibration device includes a magnetic calibration piece having a permanent magnet fixed underneath the magnetic calibration piece, wherein the magnetic calibration piece has a slit where magnetic flux of the permanent magnet leaks through.

BRIEF DESCRIPTION OF THE DRAWINGS

Objects and advantages of the invention will become apparent upon reading the following detailed description and upon reference to the accompanying drawings in which:

FIG. 2 is a schematic view of a sensor bracket employed in a system according to an aspect of the present disclosure.

FIG. 3A is an enlarged view of a magnetic calibration piece in a system according to an aspect of the present disclosure.

FIG. 3B is a cross-sectional view of a portion of the calibration piece of FIG. 3A.

DETAILED DESCRIPTION

In the following Detailed Description, reference is made to the accompanying drawings, which form a part hereof, and in which is shown by way of illustration specific embodiments in which the invention may be practiced. The drawings show illustrations in accordance with examples of embodiments, which are also referred to herein as "examples". The drawings are described in enough detail to enable those skilled in the art to practice the present subject matter. Because components of embodiments of the present invention can be positioned in a number of different orientations, directional terminology is used for purposes of illustration and is in no way limiting. It is to be understood that other embodiments may be utilized and structural or logical changes may be made without departing from the scope of the present invention.

In this document, the terms "a" and "an" are used, as is common in patent documents, to include one or more than one. In this document, the term "or" is used to refer to a nonexclusive "or," such that "A or B" includes "A but not B," "B but not A," and "A and B," unless otherwise indicated. The following detailed description, therefore, is not to be taken in a limiting sense, and the scope of the present invention is defined by the appended claims.

For an electromagnet or permanent magnet array as workpiece, the conventional metrology system lacks an off-the-shelf solution that can obtain optical images, three-dimensional magnetic field and height topology maps of the workpiece and provide data from the optical field, magnetic field and height information in order to correlate defects in the manufacturing process of the workpiece. Aspects of this disclosure relate to a metrology system configured to provide visual inspection of the workpiece (e.g., obtain high resolution optical images), three-dimensional magnetic field map, and height measurement (i.e., workpiece topology mapping). Specifically, an optical inspection tool provides images of the sample, a 3D Hall probe (or other type of magnetic sensors) provides simultaneous x,y,z field information, and a capacitive sensor (or other type of height sensors) provides the sample height information. A software controlled mechanical stage is used to bring sample points of interest under the desired tool for measurement. The metrology system according to the embodiments includes a calibration device/method to verify stage fiducials in x, y, z positions. The optical field, magnetic field, and height information can all be used independently or together in order to correlate defects in the manufacturing process of the workpiece. According to the embodiments of the disclosure, for a magnetic workpiece, the magnetic field in three dimensions at a given position, the height information at that position and an image of those features can be obtained.

Figure 1A:
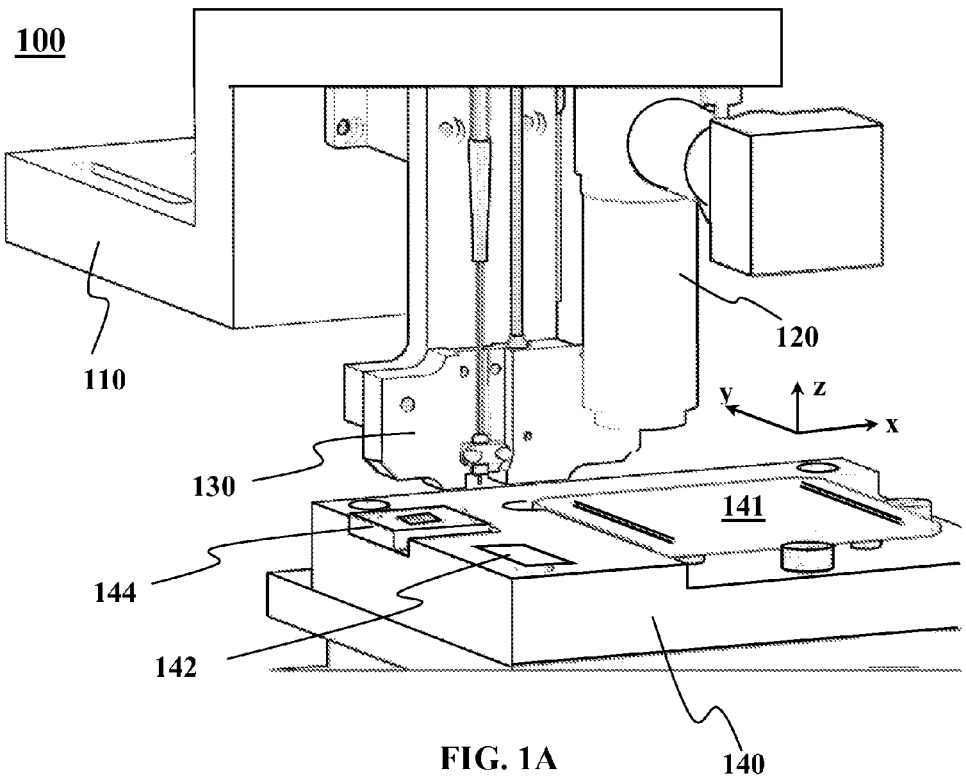
FIG. 1A is a three-dimensional view of a metrology system according to an aspect of the present disclosure.
Figure 1B:
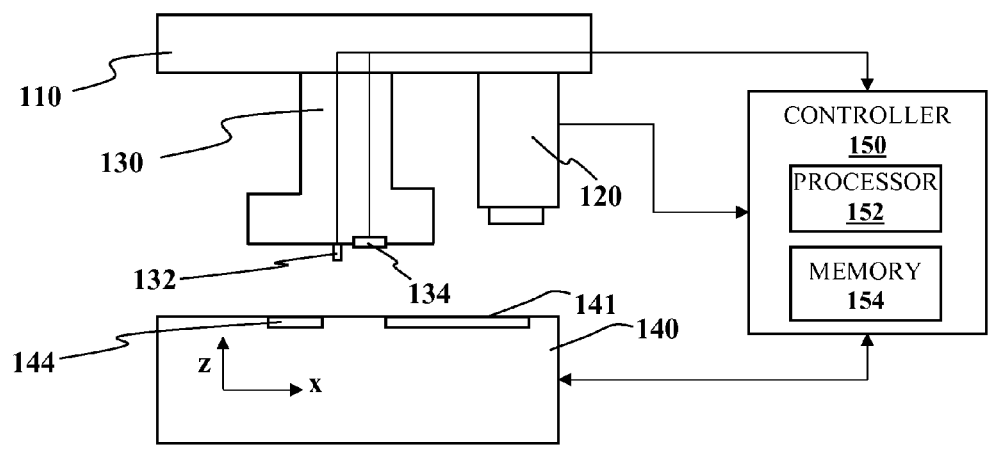
FIG. 1B is a schematic view of a metrology system according to an aspect of the present disclosure.

As seen in FIGS. 1A-1B, a metrology system 100 according to an aspect of the present disclosure may include a system head 110 to which is mounted and an optical inspection tool 120 and a sensor bracket 130 held by the system head 110. The sensor bracket 130 includes a magnetic sensor 132, (e.g., a Hall probe) and a height sensor 134 (e.g., a capacitive sensor) as shown in FIG. 2. The metrology system 100 further includes a stage 140 for holding the workpiece (e.g., a magnet array) 141. The workpiece may include features that are either co-planar or not co-planar.

The stage 140 and system head 110 are configured for relative movement with respect to each other. By way of example, and not by way of limitation, the stage 140 may be configured to move the workpiece 141 in x, y, and (optionally) z directions. By way of example, the stage 140 may include suitably configured bearings that allow the stage to move along x, y and z directions and corresponding actuators that impart movement to the stage along these directions in response to input signals. Furthermore, the stage 140 may include position sensing mechanisms that can sense the relative position of the stage with respect to the x, y, and z axes and produce corresponding output signals. The positioning and sensing mechanisms may provide the stage 140 with sub-micron resolution in the X, Y, and Z directions. By way of example, the positioning mechanisms may provide the stage with resolution in the X-Y position of about 5 nanometers (nm) or better and resolution of about 20 nm or better in the Z position.

In the example above, the system head 110 may be fixed while the stage 140 is moved with respect to the system head to impart the relative movement. Alternatively, the stage may be fixed while the system head is moved relative to the stage, e.g., using bearings and actuators responsive to signals from the controller 150 to impart the relative movement. In yet other implementations, both the system head 110 and stage 140 may be configured to move with respect to a fixed frame to impart relative movement between the system head and the stage.

On the stage 140, there are an optical calibration slide 142 and a magnetic calibration piece 144. In the example shown in FIGS. 1A-1B, the magnetic calibration piece 144 is also configured to act as the height sensor calibration piece. However, aspects of the present disclosure include implementations in which a separate calibration piece may be included on the stage 140 for alignment of the height sensor 134. It is also possible for the magnetic calibration piece 144 to include a visible fiducial feature that can be used to align the optical inspection tool 120.

The system 100 may include a controller 150 having a processor 152 and memory 154 coupled to the optical inspection tool 120, magnetic sensor 132, height sensor 134 and the stage 140 (e.g., the actuator(s) and position sensing mechanism(s)). The system 100 may be configured to use the optical calibration slide 142 and the magnetic calibration piece 144 as fiducials to determine the relative offsets between two or more of the optical inspection tool 120, magnetic sensor 132, and height sensor 134. By way of example, and not by way of limitation, the stage 140 may be moved with respect to the x and y directions to align each tool over its respective calibration piece. The position of the stage 140 can recorded at each alignment position and differences in the alignment positions for different sensors can provide offsets between the sensors. For example, an optical alignment position $(x_o, y_o)$ of the stage 140 may be recorded when the optical inspection tool 120 is aligned over a centering mark (e.g., a visible fiducial feature on the magnetic calibration piece 144. A magnetic alignment position $(x_m, y_m)$ may be recorded when the magnetic sensor 132 is centered over a fiducial feature on the magnetic calibration piece 144. A height alignment position $(x_h, y_h)$ may be recorded when the height sensor is 134 centered over a fiducial feature on a height calibration piece.

The processor 152 can obtain the three alignment positions from position sensors on the stage 140 and calculate an offset $\Delta_{mo}$ between the magnetic sensor 132 and the optical inspection tool 120 as $\Delta_{mo}=(x_o-x_m, y_o-y_m)$ and an offset $\Delta_{ho}$ between the height sensor 134 and the optical inspection tool 120 as $\Delta_{ho}=(x_o-x_h, y_o-y_h)$. During measurements of the workpiece 141, the stage 140 is translated as signals from the optical inspection tool, magnetic sensor, and height sensor are recorded as functions of stage position. Positions of the optical inspection tool, magnetic sensor and height sensor can be correlated to the stage position by applying the appropriate offset(s). Those skilled in the art will be able to devise suitable modifications to the above-described procedure to address situations where spatially separate fiducial features are used for aligning two or more of the optical inspection tool 120, magnetic sensor 132, and height sensor 134. For example, a separate fiducial feature on the optical calibration slide 142 may be used to align the optical inspection tool. This fiducial feature may have a known displacement $(\Delta x, \Delta y)$ with respect to the fiducial feature on the magnetic calibration piece that is used to align the magnetic sensor 132 and height sensor 134. In such a case the offset $\Delta_{mo}$ may be calculated as $\Delta_{mo}=(x_o-x_m+\Delta x, y_o-y_m+\Delta y)$ and the offset $\Delta_{ho}$ may be similarly calculated as $\Delta_{ho}=(x_o-x_h+\Delta x, y_o-y_h+\Delta y)$.

The optical inspection tool 120 may be used to obtain high resolution optical images. By way of example but not by way of limitation, the optical inspection tool 120 may be an optical microscope, a scanning capacitance microscope (SCM), or electron microscope such as critical dimension-scanning electron microscope (CD-SEM). In one example, the optical inspection tool 120 is an Edmund Optics optical microscope (1.3 Megapixel CCD, EO-1312C) with 2× and 5× long working distance objectives and co-axial illumination. The objectives have an optical blur of 5 µm and 2 µm for the 2× and 5× lens, respectively. The microscope is supported by optical post-processing for feature recognition and feature size extraction. Additionally, the 2× and 5× lens have different fields of view, and thus, it will be advantageous to use the 5× lens for higher resolution inspection versus the 2× lens.

The magnetic sensor 132 may include a Hall probe configured to sense the magnetic flux density that is present in a given area. A Hall probe is usually a wand-shaped device placed at or near the surface of the magnet and reads the magnetic flux density in that area. The Hall probe is connected to a flux density meter or a gaussmeter, which converts the magnetic flux readings collected from the Hall probe into a voltage. The voltage is proportional to the magnitude of the magnetic field in that given area. In one embodiment, the magnetic sensor 132 may be a Hall probe (or other magnetic sensor) having a minimum resolution of 10 microns in the field and may be positioned on a workpiece to within 5-10 microns. In one embodiment, the magnetic sensor 132 may measure magnetic field to within 2 Gauss. Moreover, an optional temperature sensing function may be built into the magnetic sensor to facilitate calibration of temperature-dependent performance. In one example, the magnetic sensor 132 may be a Senis three-axis Hall transducer with 10 µm×150 um×150 µm spatial resolution, ±1 T measurement range and sensitivity of 2 G at 14 bits. The Senis field transducer has a differential signal output of ±10 V per axis in addition to a temperature sensing output for a total of 7 outputs. A differential-to-single ended converter is used to reduce the connections to accommodate the limited general purpose input/output (GPIO) connections on the stage. These transducers are pre-calibrated prior to installation for different field ranges and resolution requirements. In alternative embodiments, the magnetic sensor 132 may some other type of magnetic sensor, such as a magnetoresistive sensor, giant magnetoresistance sensor (GMR), or magneto optical Kerr effect (MOKE).

The height sensor 134 is used for height mapping of a workpiece. In one embodiment, the height sensor 134 is a capacitive sensor having nm-scale resolution in the height. In addition, the X-Y position of the height sensor 134 may be located to within slit dimensions (typically 50-100 microns). In one embodiment, the height sensor 134 may be a MicroSense capacitive displacement sensor with 250 µm standoff and ±125 µm measurement range. The resolution is 15 nm at 1 kHz bandwidth. The output signal is ±10 V with 0 V corresponding to the standoff distance of 250 µm. Like Hall probes, capacitive sensors can be pre-calibrated to a desired working range. In alternative embodiments, the height sensor 134 may be a laser interferometer, inductive sensor, drop gauge, atomic force microscope (AFM), scanning tunneling microscope (STM), or stylus profilometer.

The system head position can be determined by the stage 140. The optical inspection tool 120, the magnetic sensor 132 and the height sensor 134 are in different locations and thus position calibration for these tools is required. The positions of the optical inspection tool 120, magnetic sensor 132 and the height sensor 134 can be cross-referenced using offsets determined from one or more fiducial features the stage 140, such as the optical calibration slide 142 and/or magnetic calibration piece 144. In addition, the sizes of features in images obtained with the optical inspection tool 120 or distances between such features can be calibrated using the optical calibration slide. The apparent size of features of known size on the optical calibration slide can be measured in pixels in an image of these features obtained with the optical inspection tool. The ratio of the apparent size to the known size can be used to provide a calibration factor to determine the actual size of other features in the image or the actual distance between two or more such features, e.g., by converting pixels to distances. By way of example, and not by way of limitation, the optical calibration slide 142 may include features of known dimension (e.g., circles of known diameter) for such calibration of the optical inspection tool 120.

In some implementations, the optical inspection tool 120 may be an optical microscope having an objective with both brightfield and darkfield capability. In brightfield microscopy, the sample is illuminated, direct illumination is collected and the image is formed as a result of absorption of illumination by the sample. In darkfield microscopy, direct illumination is blocked from being collected by the objective and the image is formed by illumination scattered by the sample. According to aspects of the present disclosure, the same calibration method described above may be used for calibration in both brightfield and darkfield modes. The calibration values for brightfield and darkfield modes may differ.

FIGS. 3A-3B illustrate a possible configuration for the magnetic calibration piece 144 on the stage 140. In one embodiment, the magnetic calibration piece 144 includes a magnet 146 sandwiched between top and bottom plates 147, 149 made of stainless steel. The top plate 147 has across-shaped opening/slit 145. The slit 145 may include two slits 145$_x$, 145$_y$ respectively aligned with the x and y axes in a cross or "L" shape. A magnetic flux of the permanent magnet 146 leaks through the slit 145. A position calibration for the Hall probe 132 can be obtained by measuring the magnetic field as a function of X-Y position and identifying the coordinates of the magnetic alignment position ($x_m$, $y_m$) from the zero crossing in the vertical composition of the magnetic field. For example, $x_m$ is the location where $B_z(x)=0$ in the example shown in FIG. 4. In one embodiment, the magnetic calibration piece 144 consists of an XY corner fiducial with 50-100 µm wide features that can be seen optically. The corner fiducials or the slit 145 may provide a fiducial feature for alignment the optical inspection system 120.

Figure 4:
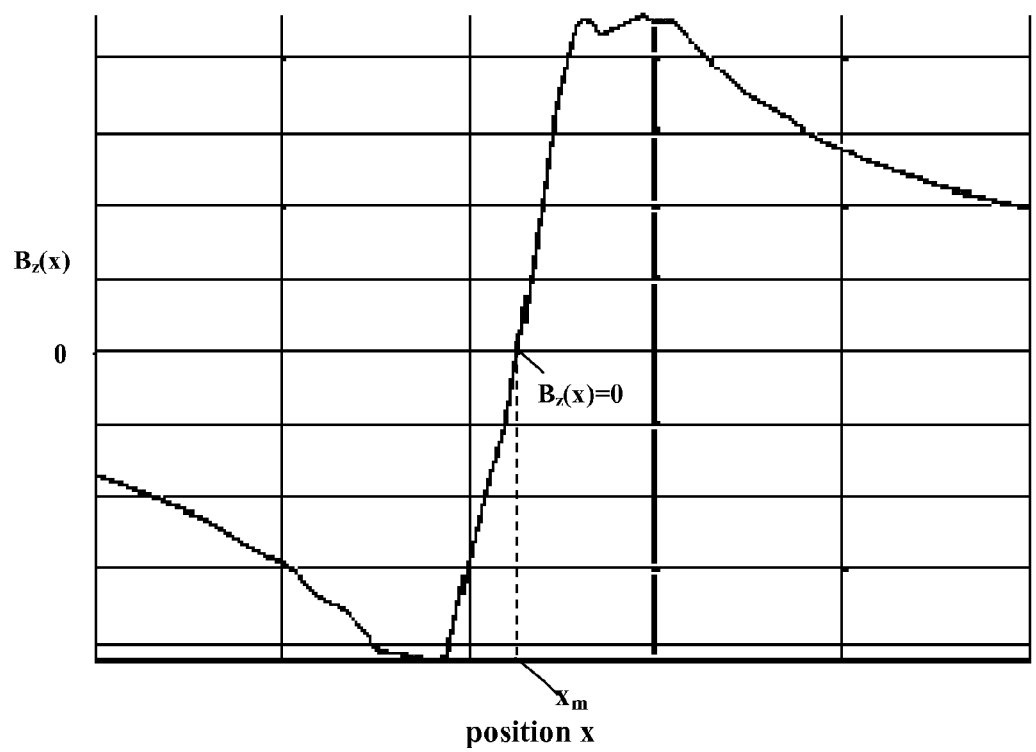
FIG. 4 is a graph showing a vertical magnetic field measured from a magnetic calibration piece in a system according to an aspect of the present disclosure.

In some implementations, the magnetic calibration piece 144 may also serve as a calibration piece for the height sensor 134. For example, as the height sensor 134, (e.g., a capacitive sensor) is moved over the slit 145 the signal from the height sensor abruptly changes as it passes over the slit. In addition, when the magnetic sensor 132 sweeps across the slit 145, the magnetic alignment position ($x_m$, $y_m$) can be extracted from the zero crossing in a plot of the field slope, e.g., as shown in FIG. 4. In a similar manner, the height alignment position ($x_h$, $y_h$) can be determined from an abrupt change in the height sensor signal as the height sensor 134 passes over the same slit 145. The slit 145, can also be used as a fiducial feature for determining the optical alignment position ($x_o$,$y_o$) for alignment of the optical inspection tool 120. This simplifies the calculation of the offsets of the magnetic sensor 132 and the height sensor 134 with respect to the optical inspection tool.

A metrology system according to an aspect of the present disclosure may collect optical images of a workpiece (e.g., a magnet array) as a function of sample position, i.e., Image(x, y), magnetic field information in the form of x, y and z components as a function of sample position, i.e., Bfield(x,y,z), and height information as a function of sample position, i.e., Height (x, y). In addition, the above discussed fiducial features can be used to account for physical offsets between these tools to ensure correlation between the optical, magnetic and height data sets. In addition, a metrology system according to an aspect of the present disclosure may have a large sampling volume, for example, of 300 mm×400 mm×5 mm depending on the stage motion.

The appended claims are not to be interpreted as including means-plus-function limitations, unless such a limitation is explicitly recited in a given claim using the phrase "means for." Any element in a claim that does not explicitly state "means for" performing a specified function, is not to be interpreted as a "means" or "step" clause as specified in 35 USC §112, ¶6. In particular, the use of "step of" in the claims herein is not intended to invoke the provisions of 35 USC §112, ¶6.

What is claimed is:

1. A system, comprising:
   an optical inspection tool configured to provide image information of a sample by analyzing an image obtained by the optical inspection tool;
   a magnetic sensor configured to provide magnetic field information of the sample;
   a height sensor configured to provide height information of the sample, wherein the optical inspection tool, the magnetic sensor and the height sensor are mounted to a system head;
   a stage configured to hold the sample, wherein the stage and system head are configured to move relative to each other, wherein the stage includes one or more fiducial features, the one or more fiducial features including an optical fiducial feature that is detectable in an image obtained by the optical inspection tool when the optical inspection tool is aligned with respect to the optical fiducial feature, a magnetic fiducial feature detectable by the magnetic sensor when the magnetic sensor is aligned with respect to the magnetic feature and a height fiducial feature that is detectable by the height sensor when the height sensor is aligned with respect to the height fiducial feature.

2. The system of claim 1, further comprising a processor coupled to the optical inspection tool, the magnetic sensor, and the height sensor, wherein the processor is configured to collect the image information, the magnetic field information and the height information of the sample and use alignment information from the one or more fiducial features to determine one or more relative offsets between two or more of the optical inspection tool, the magnetic sensor, and the height sensors.

3. The system of claim 2, wherein the processor is configured to use the one or more relative offsets to obtain magnetic field and sample height information at a given position on the sample.

4. The system of claim 1, wherein the optical inspection tool is an optical microscope.

5. The system of claim 1, wherein the magnetic sensor is a Hall probe.

6. The system of claim 1, wherein the magnetic sensor has a temperature sensing function.

7. The system of claim 1, wherein the height sensor is a capacitive sensor.

8. The system of claim 1, wherein the magnetic sensor and the height sensor are provided in a bracket mounted on the system head.

9. The system of claim 1, wherein the optical fiducial feature includes an optical calibration slide having features of known dimension that are detectable by the optical inspection tool.

10. The system of claim 1, wherein the magnetic fiducial feature includes a magnetic calibration piece having a permanent magnet fixed underneath the magnetic calibration piece, wherein the magnetic calibration piece has one or more slits through which a magnetic flux of the permanent magnet leaks.

11. The system of claim 10, wherein the one or more slits are also part of the optical fiducial feature.

12. The system of claim 10, wherein the one or more slits are also part of the height fiducial feature.

13. The system of claim 10, wherein the one or more slits are also part of the optical fiducial feature and also part of the height fiducial feature.

14. A method, comprising:
imparting relative movement between a stage which holds a sample and a system head, wherein an optical inspection tool configured to obtain images of the sample, a magnetic sensor and a height sensor are mounted to the system head; and
determining relative positions of the optical inspection tool, the magnetic sensor and the height sensor with respect to one or more fiducial features on the stage, the one or more fiducial features including an optical fiducial feature that is detectable in an image obtained by the optical inspection tool when the optical inspection tool is aligned with respect to the optical fiducial feature, a magnetic fiducial feature detectable by the magnetic sensor when the magnetic sensor is aligned with respect to the magnetic feature and a height fiducial feature that is detectable by the height sensor when the height sensor is aligned with respect to the height fiducial feature.

15. The method of claim 14, further comprising using the relative positions determined with the one or more fiducial features to determine one or more relative offsets between two or more of the optical inspection tool, the magnetic sensor, and the height sensor.

16. The method of claim 15, further comprising:
acquiring image information of the sample with the optical inspection tool;
acquiring magnetic field information of the sample with the magnetic sensor;
acquiring height information of the sample with the height sensor; and
using the or more relative offsets to obtain magnetic field and sample height information at a given position on the sample.

17. The method of claim 14, wherein the magnetic sensor and the height sensor are provided in a bracket mounted on the system head.

18. The method of claim 14, wherein the optical fiducial feature includes an optical calibration slide having circles of known dimension for position calibration for the optical inspection tool.

19. The method of claim 14, wherein the magnetic calibration feature includes a magnetic calibration piece having a permanent magnet fixed underneath the magnetic calibration piece, wherein the magnetic calibration piece has one or more slits through which a magnetic flux of the permanent magnet leaks.

20. The method of claim 19, wherein the one or more slits are also part of the optical fiducial feature.

21. The method of claim 19, wherein the one or more slits are also part of the height fiducial feature.

22. The method of claim 19, wherein the one or more slits are also part of the optical fiducial feature and also part of the height fiducial feature.

* * * * *